(12) United States Patent
Bhargava et al.

(10) Patent No.: US 7,998,973 B2
(45) Date of Patent: Aug. 16, 2011

(54) TIVOZANIB AND TEMSIROLIMUS IN COMBINATION

(75) Inventors: Pankaj Bhargava, Newton, MA (US); W. Brooke Esteves, Westford, MA (US); John L. Ryan, Philadelphia, PA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/856,414

(22) Filed: Aug. 13, 2010

(65) Prior Publication Data

US 2011/0118297 A1 May 19, 2011

Related U.S. Application Data

(60) Provisional application No. 61/261,252, filed on Nov. 13, 2009.

(51) Int. Cl.
*C07D 261/14* (2006.01)
*C07D 261/04* (2006.01)
*C07D 221/02* (2006.01)
*C07D 405/00* (2006.01)
*C07D 213/46* (2006.01)
*A01N 43/42* (2006.01)
*A61K 31/44* (2006.01)

(52) U.S. Cl. ..... 514/299; 514/354; 546/183; 546/282.1; 546/340; 548/246

(58) Field of Classification Search ............. 514/299, 514/354; 546/183, 282.1, 340; 548/246
See application file for complete search history.

(56) References Cited

U.S. PATENT DOCUMENTS

| 6,821,987 B2 | 11/2004 | Kubo et al. |
| 2006/0052415 A1 | 3/2006 | Matsunaga et al. |
| 2006/0094674 A1 | 5/2006 | Neel et al. |
| 2007/0105887 A1 * | 5/2007 | Moore ............... 514/291 |

OTHER PUBLICATIONS

Atkins et al. 2004, Randomized Phase II Study of Multiple dose levels of CCI-779, a novel mTOR kinase inhibitor, in patients with advanced refractory renal cell carcinoma. Journal of Clinical Oncology, vol. 22, No. 5, pp. 909-918.*
Eskens et al. "An open label phase I dose escalation study of KRN951, a tyrosine kinase inhibitor of vascular endothelial growth fractor receptor 2 and 1 in a 4 week on, 2 week off schedule in patients with advanced . . . ." Journal of Clinical Oncology, 2006 ASCO Annual Meeting Proceedings Part I, vol. 24, No. 18S (Jun. 20 Supplement), 2006, p. 2034.*
AVEO press release dated Apr. 14, 2008 "AVEO Pharmaceuticals' novel triple VEGF Receptor inhibitor shows tumor regression in Patients with advanced renal cancer".*
Campas et al. Oct. 2009, "Tivozanib (AV-951, KRN-951)" Drugs of the Future, 34(10), pp. 793-796.*
Eskens et al. Nov. 2006, "Phase I and pharmacological study of KRN951, a potent VEGFR tyrosine kinase inhibitor given in a 4 week on, 2 week." Eur J Cancer Suppl (18th EORTC-NCI-AACR Symp Mol Targets Cancer Ther), 4(12), abstract 38.*
Robinson et al. Oct. 2008, "Combination treatment of VEGFR inhibitor AV-951 and rapamycin reveals distinct mechanisms of each agent's anti-tumor activity" Eur J Cancer Suppl (20th EORTC-NCI-AACR Symp Mol Targents Cancer Ther), 6(12), abstract 53.*
AVEO Pharmaceuticals, Inc., Jan. 31, 2008 Press Release (2 pages).
AVEO Pharmaceuticals, Inc., May 29, 2009 Press Release (3 pages).
Bhargava et al., "Updated Activity and Safety Results of a Phase II Randomized Discontinuation Trial (RDT) of AV-951, a Potent and Selective VEGFR1, 2, and 3 Kinase Inhibitor, in Patients with Renal Cell Carcinoma (RCC)," *American Society of Clinical Oncology, J Clin Oncol 27*:15s, 2009 (suppl; abstr 5032) (4 pages).
Patel et al., "Phase I Study Combining Treatment with Temsirolimus and Sunitinib Malate in Patients with Advanced Renal Cell Carcinoma," *Clinical Genitourinary Cancer*, vol. 7, No. 1, pp. 24-27, 2009.
Patnaik et al., "A Phase I, Pharmacokinetic and Pharmacodynamic Study of Sorafenib (S), a Multi-Targeted Kinase Inhibitor in Combination with Temsirolimus (T), an mTOR Inhibitor in Patients with Advanced Solid Malignancies." *Journal of Clinical Oncology*, 2007 ASCO Annual Meeting Proceedings (Post-Meeting Edition), vol. 25, No. 185 (Jun. 20 Supplement), 2007: 3512.
Sosman et al., "Combination Targeted Therapy in Advanced Renal Cell Carcinoma," *Cancer* 2009, 115 (10 Suppl): 2368-2375.
AVEO Pharmaceuticals, "A Phase Ib, Open-Label, Dose-Finding Study to Evaluate the Safety of AV-951 in Combination with Temsirolimus in Subjects with Metastatic Renal Cell Carcinoma," ClinicalTrials.gov Archive [online] Feb. 23, 2009 [retrieved on Mar. 8, 2001]. Retrieved from the internet <URL: http://clinicaltrials.gov/archive/NCT00563147/2009_02_23]; pp. 1-4.
AVEO Pharmaceuticals, "A Phase 2, Placebo-Controlled, Randomized, Discontinuation Trial of AV-951 in Patients with Renal Cell Carcinoma," ClinicalTrials.gov Archive [online] Apr. 9, 2008 [retrieved on Mar. 9, 2001]. Retrieved from the internet <URL: http://clinicaltrials.gov/archive/NCT00502307/2008_04_09]; pp. 1-3.
Sanders, "New Drug Bulletin: Temsirolimus (Torisel-Wyeth)," University of Utah Hospitals & Clinics [online], Sep. 14, 2007 [retrieved on Mar. 8, 2011]. Retrieved from the internet <URL: healthcare.utah.edu/pharmacy/bulletins/NDB_139.pdf; pp. 1-2.
Fishman et al., "Abstract B60: Combination of tivozanib (AV-951) and temsirolimus in pateitns with renal cell carcinoma (RCC): Preliminary results from a phase 1 trial," (Dec. 2009), Molecular Cancer Therapeutics: vol. 8, Issue 12, Supplement 1, Abstract B60.
International Search Report and Written Opinion dated Apr. 1, 2011.

* cited by examiner

*Primary Examiner* — Sreeni Padmanabhan
*Assistant Examiner* — Kara R McMillian
(74) *Attorney, Agent, or Firm* — Goodwin Procter LLP

(57) ABSTRACT

A method of treating a tumor in a human patient is disclosed. The method comprises co-administering to the patient: (a) a dose of 1.5 mg tivozanib per day; and (b) a dose of 25 mg temsirolimus per week. In some embodiments of the invention, the tivozanib is administered on a repeating schedule of one dose per day for three weeks, followed by one week without tivozanib administration. The disclosed method is particularly suitable for treatment of renal cell carcinoma.

4 Claims, No Drawings

TIVOZANIB AND TEMSIROLIMUS IN COMBINATION

CROSS-REFERENCE TO RELATED APPLICATION

This application claims priority to and the benefit of U.S. Provisional Application Ser. No. 61/261,252, filed Nov. 13, 2009; the entire contents of which are incorporated herein by reference.

FIELD OF THE INVENTION

The field of the invention is medicine, oncology, tyrosine kinase inhibitors, VEGF receptor inhibitors, mTOR inhibitors, and pharmaceuticals.

BACKGROUND OF THE INVENTION

Tivozanib (also known as AV-951 and KRN951) is a potent and selective small-molecule inhibitor of VEGF receptors 1, 2 and 3. Tivozanib exhibits picomolar inhibitory activity against all three receptors, and it exhibits antitumor activity in preclinical models (Nakamura et al., 2006, Cancer Res. 66:9134-9142). Tivozanib has yielded positive interim results in a 272-patient Phase 2 clinical trial (Bhargava et al., 2009, ASCO Annual Meeting Proceedings, Vol 27, No. 15s, Abstract No. 5032). The most common side effects associated with tivozanib treatment in Phase 1 and Phase 2 clinical trials are hypertension and dysphonia.

Mammalian target of rapamycin, commonly known as mTOR (also known as FRAP, RAFT1 and RAP1) is a kinase that acts downstream of activated PI3K. Several specific inhibitors of mTOR are known, including rapamycin, temsirolimus, everolimus and OSI-027. In recent years, temsirolimus (TORISEL®; also known as CCI-779) and everolimus (AFINITOR®; also known as RAD-001) have received FDA marketing approval as monotherapies for renal cell carcinoma. As a monotherapy, temsirolimus typically is administered by intravenous infusion on a weekly schedule. The side effects of temsirolimus can be severe, including severe allergic reactions, black or bloody stools, calf pain, chest pain, cough, difficult or painful urination, irregular heartbeat, fever, chills, breathing problems, severe headache, severe stomach pain or diarrhea, ulceration of mucous membranes, severe tiredness or weakness, swelling of the hands, feet or ankles, and symptoms of high blood sugar.

With any drug, optimal dosage involves balancing the desired therapeutic effect against unwanted side effects, i.e., drug toxicities. The dosage range that yields a therapeutic effect with an acceptable side effect profile is known as the therapeutic window. When two drugs are used in combination, the situation with respect to therapeutic window can become complicated and unpredictable. The therapeutic effects of the two drugs can be non-additive, additive or synergistic. Similarly, the unwanted side effects, i.e., the drug toxicities, can be non-additive, additive or synergistic.

Although the prior art contains suggestions regarding the theoretical advantages of a combination therapy involving a VEGF tyrosine kinase inhibitor and an mTOR inhibitor, the combination of a VEGF tyrosine kinase inhibitor and temsirolimus has been problematic, because of toxicity of the combination. To date, no combination of a VEGF tyrosine kinase inhibitor with temsirolimus has been found clinically tolerable at the respective individual maximum tolerated dosages (MTDs) of the drugs. For example, in 2007, Patnaik et al. reported that the combination of sorafenib and temsirolimus resulted in "significant mucocutaneous toxicity at full doses of sorafenib" (Patnaik et al., ASCO Annual Meeting Proceedings Part I, Vol. 25, No. 18S (June 20 Supplement), 2007: 3512). In 2009, Patel et al., reported dose-limiting toxicities in two out of three patients in the first cohort of patients in a trial to determine the MTDs of the sunitinib and temsirolimus in combination to treat advanced renal cell carcinoma (Patel et al., 2009, Clinical Genitourinary Cancer 7:24-27). Based on this study, Patel et al. concluded: "Concomitant use of IV temsirolimus 15 mg weekly and oral sunitinib 25 mg daily (4 weeks on, 2 weeks off) is not recommended." In a 2009 review article, Sosman et al. state that the combination of temsirolimus with sorafenib has required dose reductions, and that temsirolimus and sunitinib "are not safe to be given together" (Sosman et al., 2009, Cancer 115:2368-2375, at 2371).

SUMMARY OF THE INVENTION

The invention is based, in part, on human clinical data demonstrating that tivozanib, a VEGF tyrosine kinase inhibitor, and temsirolimus can be combined safely in human cancer patients, with each drug being administered at its previously established maximum tolerated dose. This finding is surprising because previous studies have suggested that VEGF tyrosine kinase inhibitors cannot be safely co-administered with temsirolimus. The invention provides a method of treating a tumor in a human patient, comprising co-administering to the patient: (a) a dose of 1.5 mg tivozanib per day; and (b) a dose of 25 mg temsirolimus per week. In some embodiments of the invention, tivozanib is administered on a repeating schedule of one dose per day for three weeks, followed by one week without tivozanib administration. In preferred embodiments of the invention, the tumor is a renal cell carcinoma.

DETAILED DESCRIPTION OF THE INVENTION

The invention relates to methods of (i) reducing tumor growth and (ii) increasing the efficacy and survival rates of patients suffering from solid tumor cancers, e.g., renal cell carcinoma, colorectal tumors, and neuroendocrine tumors. The disclosed methods are based on a combination therapy where tivozanib, a VEGF tyrosine kinase inhibitor, is administered with temsirolimus, a mTOR inhibitor. The disclosed methods surprisingly use tivozanib and temsirolimus each at its respective MTD despite previous studies finding that the combination of other VEGF tyrosine kinase inhibitors with temsirolimus was not clinically tolerable.

I. DEFINITIONS

For convenience, certain terms in the specification, examples, and appended claims are collected in this section.

As used herein, "combination therapy," means co-administering tivozanib and temsirolimus as part of a specific dosage regimen intended to provide the beneficial effect from the co-action of these therapeutic agents. Administration of these therapeutic agents in combination typically is carried out over a defined time period (e.g., weeks or months). Combination therapy includes administration of the therapeutic agents in a concurrent manner, e.g., the therapeutic agents can be administered at the same or a different time and can be administered by the same route or by different routes. Concurrent administration of each therapeutic agent can be effected by any appropriate route. For example, tivozanib can be administered orally while temsirolimus is administered intravenously.

As used herein, "pharmaceutically acceptable" or "pharmacologically acceptable" mean molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein, "tivozanib" means N-{2-chloro-4-[(6,7-dimethoxy-4-quinolyl)oxy]-phenyl}-N'-(5-methyl-3-isoxazolyl)urea and having the following chemical structure:

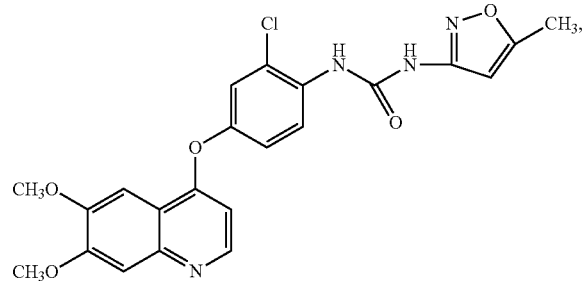

including pharmaceutically acceptable salts, esters, or polymorphs thereof. See, for example, U.S. Pat. Nos. 6,821,987 and 7,211,587, each of which are incorporated herein by reference in their entirety.

As used herein, "temsirolimus" means 42-(3-hydroxy-2-(hydroxymethyl)-2-methylpropanoate) rapamycin, which has the structure shown below:

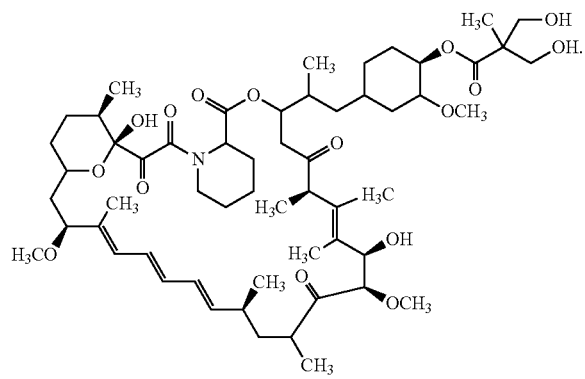

See, for example, U.S. Pat. No. 5,362,718, which is incorporated herein by reference in its entirety. Temsirolimus (TORISEL®) is also known as CCI-779. TORISEL® is available commercially from Wyeth.

II. METHODS OF THE INVENTION

The concurrent administration of tivozanib and temsirolimus can be by concurrent administration of separate formulations, i.e., a tivozanib formulation and a temsirolimus formulation. With respect to the present invention, administration of separate formulations is "concurrent" if the timing of their administration is such that the pharmacological activities of tivozanib and temsirolimus overlap in time, thereby exerting a combined antitumor effect in the patient. In the context of the present invention, concurrent administration, i.e., combination therapy, does not require the two drugs to be administered simultaneously, nor to be administered by the same route of administration, nor to be present in the body of the patient at the same time. The temporal overlap of the pharmacological activities of tivozanib and temsirolimus will depend on factors including (with respect to each of the two drugs): dosage, frequency and timing of administration, half-life, and pharmacokinetics.

The half-life of tivozanib in the human body is in the range of 3.8-4.7 days. Tivozanib accumulates in the serum after chronic dosing to a degree that would be expected based on its half-life. Serum levels reach steady state after about 2-3 weeks.

The half-life of temsirolimus in the human body is approximately 17 hours. Temsirolimus does not appear to accumulate more than would be expected based on its half life. However, the primary metabolite of temsirolimus, i.e., sirolimus (rapamycin), has mTOR activity, has a half-life that is about three times that of the parent compound. Therefore, temsirolimus is expected to exert physiological effects after temsirolimus has been cleared.

When tivozanib and temsirolimus are administered concurrently according to the present invention, the dosage of tivozanib is 1.5 mg per day. In some embodiments of the invention, the tivozanib is administered on a repeating schedule of one capsule (e.g., a single dosage from contains 1.5 mg of tivozanib) per day for three weeks, followed by one week off (i.e., 3 weeks on, 1 week off).

When tivozanib and temsirolimus are administered concurrently according to the present invention, the dosage of temsirolimus is 25 mg per week. In some embodiments of the invention, a pharmacologically equivalent dose of sirolimus (rapamycin) is substituted for temsirolimus.

When tivozanib and temsirolimus are administered concurrently according to the present invention, the drug combination can be administered in a single formulation or as separate formulations. In some embodiments of the invention, tivozanib is administered as an oral tablet or capsule, and temsirolimus is administered as an intravenous (IV) infusion. In a preferred embodiment of the invention, tivozanib is administered as a 1.5 mg capsule on a repeating schedule of one capsule per day for three weeks, followed by one week off, while 25 mg of temsirolimus is administered by IV infusion once per week.

The method of the invention is suitable for treating various types of solid tumors, e.g., renal cell carcinoma, colorectal tumors and neuroendocrine tumors. The present invention is particularly suitable for treating renal cell carcinoma.

Examples

The invention is further illustrated by the following example. The following example is provided for illustration purposes only, and is not to be construed as limiting the scope or content of the invention in any way.

The combination of tivozanib and temsirolimus was tested in a Phase 1 clinical trial. Human patients with advanced renal cell carcinoma (with clear cell component) who had not received prior VEGF-targeted therapy or who had failed to respond in one prior VEGF-targeted therapy were candidates for enrollment. Each patient received oral tivozanib (3 weeks on, 1 week off) and intravenous temsirolimus (once weekly). In previous trials, the safety of tivozanib had been established at a dose of 1.5 mg/day when administered for four weeks followed by a two week break (4 weeks on, 2 weeks off), or when administered for three weeks followed by a one week break (3 weeks on, 1 week off). The approved dose of temsirolimus is 25 mg, once weekly. The following dose levels have been evaluated in this Phase 1 study:

| Dose Level | Tivozanib Dose | Temsirolimus Dose |
|---|---|---|
| 1 | 0.5 mg/day | 15 mg/week |
| 2 | 1.0 mg/day | 15 mg/week |
| 3 | 1.5 mg/day | 15 mg/week |
| 4-MTD Cohort | 1.5 mg/day | 25 mg/week |

Sixteen patients were enrolled in the study: 16 males and 0 females, median age 62 yrs (range 43-70), Karnofsky Performance Status (KPS) 100% (11 pts), 90% (4 pts) or 80% (2 pt). Twelve of the patients (75%) had received prior VEGF targeted therapy. The median duration of treatment was 16.8 weeks (range 0.7-51.4 weeks). Based on preliminary data, treatment-related adverse events observed in at least 20% of patients across all dose levels were: stomatitis/mucositis (38%), thrombocytopenia (31%), diarrhea (31%), fatigue/asthenia (19%), hypertension (19%), rash (10%), nausea (19%) and vomiting (19%). No dose-limiting toxicities and no grade 4 toxicities were observed. In this Phase 1 clinical trial, the MTD of the combination was tivozanib 1.5 mg/day and temsirolimus 25 mg/week. The available data indicate lack of any significant pharmacokinetic interaction between the two drugs. Two patients had a confirmed partial response. Five patients had stable disease for at least 20 weeks.

This human clinical study supports the following conclusions.

(1) The combination of tivozanib with temsirolimus is well tolerated in human patients with advanced renal cell carcinoma.

(2) Tivozanib is the first VEGF tyrosine kinase inhibitor that can be combined with temsirolimus at full doses of both agents: 1.5 mg/day tivozanib and 25 mg/week temsirolimus.

(3) The combination of Tivozanib and temsirolimus shows encouraging clinical activity in patients with advanced renal cancer, including patients who have failed prior therapy with commercially available drugs for this disease.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

We claim:

1. A method of treating a tumor in a patient, comprising co-administering to the patient: (a) a dose of 1.5 mg tivozanib per day; and (b) a dose of 25 mg temsirolimus per week.

2. The method of claim 1, wherein tivozanib is administered on a repeating schedule of one dose per day for three weeks, followed by one week without tivozanib administration.

3. The method of claim 1, wherein the tumor is selected from the group consisting of: a renal cell carcinoma, a colorectal tumor, and a neuroendocrine tumor.

4. The method of claim 1, wherein the tumor is a renal cell carcinoma.

* * * * *